(12) United States Patent
Molho et al.

(10) Patent No.: US 9,297,784 B2
(45) Date of Patent: Mar. 29, 2016

(54) DEVICE AND METHOD FOR EXTRACTING TARGET OBJECTS FROM A SAMPLE

(71) Applicant: CALIPER LIFE SCIENCES, INC., Hopkinton, MA (US)

(72) Inventors: Joshua I. Molho, Oakland, CA (US); Daniel G. Stearns, Los Altos Hills, CA (US); I-Jane Chen, Alameda, CA (US); Danh Tran, Hayward, CA (US); Bradley W. Rice, Danville, CA (US); Tobias Daniel Wheeler, Alameda, CA (US); Alexander V. Dukhovny, San Francisco, CA (US)

(73) Assignee: CALIPER LIFE SCIENCES, INC., Hopkinton, MA (US)

( * ) Notice: Subject to any disclaimer, the term of this patent is extended or adjusted under 35 U.S.C. 154(b) by 200 days.

(21) Appl. No.: 13/838,338

(22) Filed: Mar. 15, 2013

(65) Prior Publication Data

US 2014/0262787 A1    Sep. 18, 2014

Related U.S. Application Data

(63) Continuation-in-part of application No. 13/705,670, filed on Dec. 5, 2012.

(51) Int. Cl.
*G01N 27/447* (2006.01)
*B01L 3/00* (2006.01)

(52) U.S. Cl.
CPC .... *G01N 27/44756* (2013.01); *B01L 3/502738* (2013.01); *B01L 3/502761* (2013.01); *B01L 2200/0636* (2013.01); *B01L 2200/0652* (2013.01); *B01L 2300/0864* (2013.01); *B01L 2400/0622* (2013.01)

(58) Field of Classification Search
None
See application file for complete search history.

(56) References Cited

U.S. PATENT DOCUMENTS

| 8,162,149 | B1 | 4/2012 | Perroud et al. | |
|---|---|---|---|---|
| 2005/0019213 | A1* | 1/2005 | Kechagia et al. | 422/57 |
| 2009/0098541 | A1* | 4/2009 | Southern et al. | 435/6 |
| 2010/0003666 | A1* | 1/2010 | Lee et al. | 435/5 |

(Continued)

FOREIGN PATENT DOCUMENTS

| EP | 2153898 A1 | 2/2010 |
|---|---|---|
| EP | 2525209 A1 | 11/2012 |
| WO | 2009010719 A1 | 1/2009 |

OTHER PUBLICATIONS

Zhong et al. Lab Chip. Jan. 2008 ; 8(1): 68-74.*

(Continued)

*Primary Examiner* — Jennifer Dieterle
(74) *Attorney, Agent, or Firm* — Cardinal Law Group

(57) ABSTRACT

The invention provides devices, systems, and methods for extracting target objects from a sample. In the method, a stream of sample containing a plurality of target and non-target objects is directed by first and second streams of buffer through a sample inlet channel into a fluid junction and through the fluid junction into a sample waste channel. In response to detecting a target object within the stream of sample, an actuator is energized to close a normally open valve, resulting in a transient burst of cross-flow into the fluid junction that briefly diverts the flow of sample within the fluid junction and results in an aliquot of sample being directed into an aliquot delivery channel. The combination of the valve and the actuator acts as a self-limiting pulse generator.

13 Claims, 11 Drawing Sheets

(56) References Cited

U.S. PATENT DOCUMENTS

| | | | |
|---|---|---|---|
| 2010/0224493 A1* | 9/2010 | Davalos et al. | 204/547 |
| 2010/0240092 A1* | 9/2010 | Igata | 435/34 |
| 2010/0317093 A1* | 12/2010 | Turewicz et al. | 435/287.2 |
| 2011/0030808 A1* | 2/2011 | Chiou et al. | 137/13 |
| 2012/0236299 A1 | 9/2012 | Chiou et al. | |
| 2012/0264654 A1* | 10/2012 | Dendukuri et al. | 506/39 |
| 2013/0337500 A1* | 12/2013 | Tan et al. | 435/39 |

OTHER PUBLICATIONS

Plast-O-Matic Valves 2013.*
PCT (PCT/US2014030750) Notification of Transmittal of the International Search Report and Written Opinion of the International Searching Authority, Mailed Sep. 11, 2014, 9 pages.

* cited by examiner

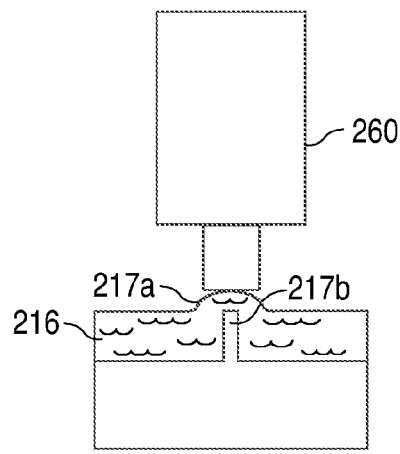 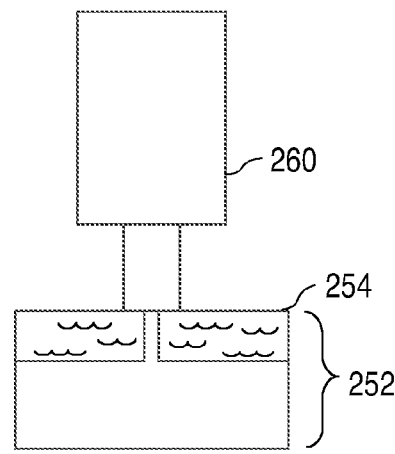
FIG. 2A　　　　FIG. 2B
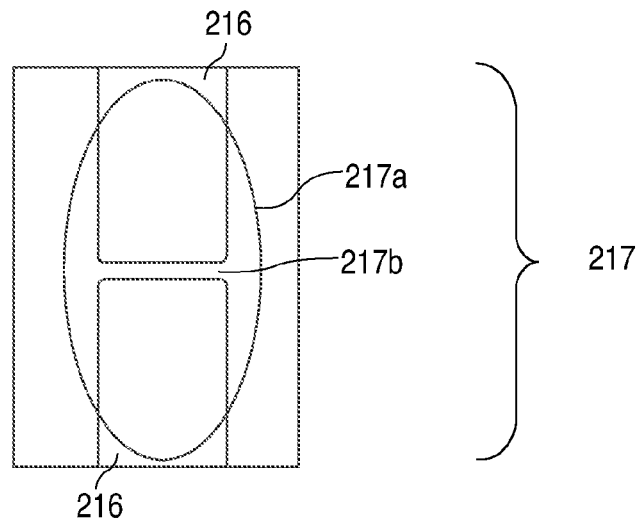
FIG. 2C
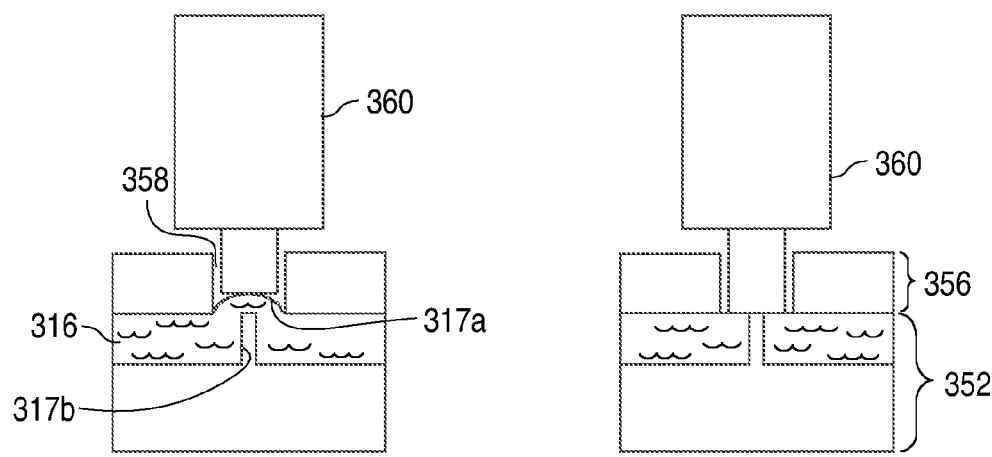
FIG. 3A　　　　FIG. 3B

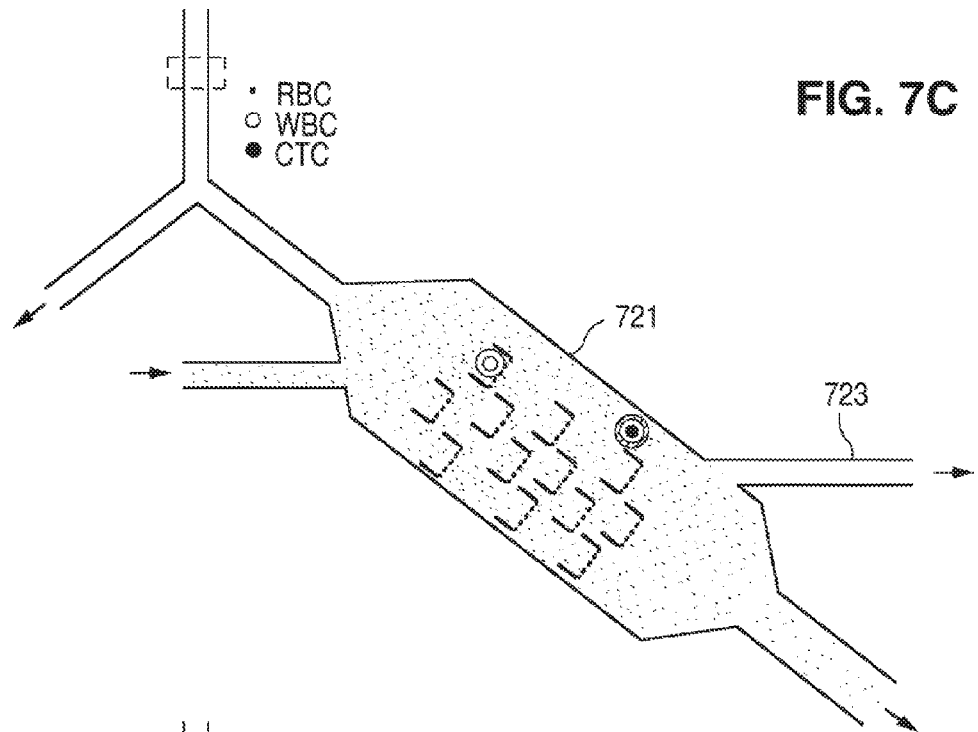
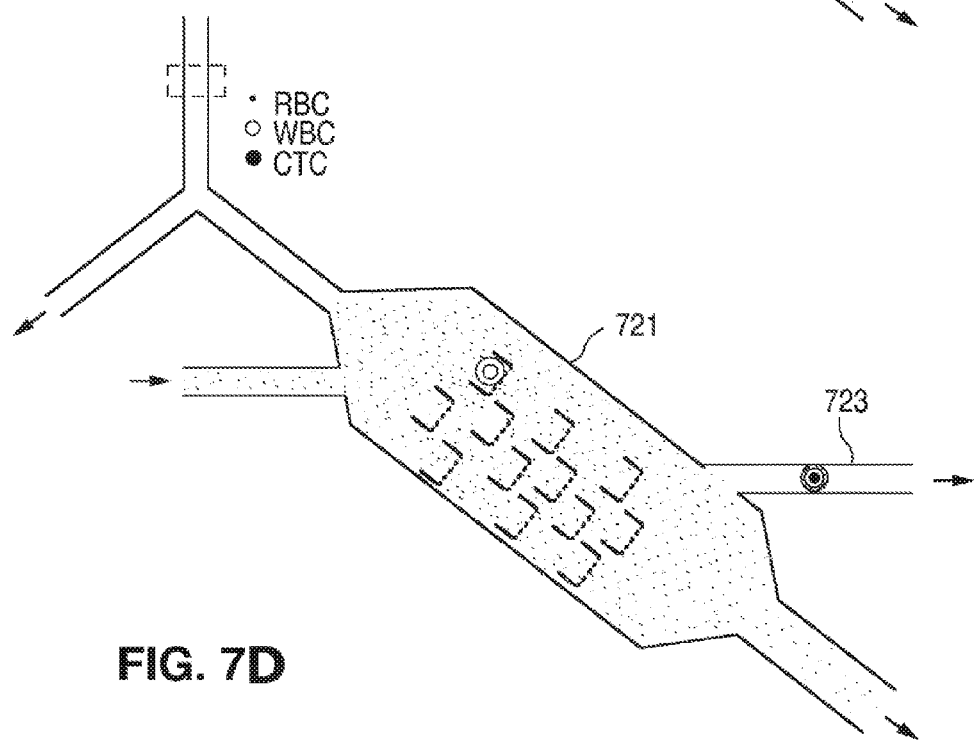

DEVICE AND METHOD FOR EXTRACTING TARGET OBJECTS FROM A SAMPLE

CROSS-REFERENCE TO RELATED APPLICATION

This application is a continuation-in-part of, and claims the benefit of, U.S. patent application Ser. No. 13/705,670 filed Dec. 5, 2012, the disclosure of which is herein incorporated by reference.

TECHNICAL FIELD

The present disclosure is in the field of microfluidic devices and methods. In particular, described herein are microfluidic devices, systems, and methods for extracting target objects such as rare cells and molecules from a sample.

BACKGROUND OF THE INVENTION

High-content analysis and isolation of cells is a growth area in personalized medicine. Both white blood cells (WBCs) and circulating tumor cells (CTCs), for example, can provide valuable information for diagnosis and treatment of diseases.

High throughput screening of WBCs can help determine whether a sick patient is responding to a specific drug or a healthy individual has mounted an adequate response to an immunization. Isolated viable WBCs can be used to determine whether specific T cell subpopulations are present in the blood and are capable of eliciting an immune response to the human immunodeficiency virus (HIV).

CTCs, i.e., tumor cells that are identified in transit within the blood stream, are shed from primary and metastatic cancers. Their isolation may be key in understanding the biology of metastasis and in a broad range of clinical applications, including early detection of cancer, the discovery of biomarkers to predict treatment responses and disease progression, as well as monitoring of minimal residual disease following and/or during treatment. Identification of CTC subsets may also allow tailoring of treatment on an individual basis.

Unfortunately, both WBCs and CTCs are present in low numbers in whole-blood samples, making their characterization and isolation problematic. Red blood cells (RBCs) typically outnumber WBCs in a whole-blood sample by a ratio of approximately 1000:1. CTCs are extraordinarily rare. An average cancer patient has approximately one to ten CTCs per milliliter of blood (one CTC for every billion blood cells).

Traditionally, gradient separations have been used to separate RBCs from various populations of WBCs. Gradient separations work on the principle that RBCs are small and dense and can form a pellet when whole blood is centrifuged. While effective, the gradient methods are typically slow, difficult to automate, and produce cells with poor viability.

Fluorescence activated cell sorting (FACS) is a well established technique for isolating CTCs from a large population of cells. However, to collect a significant sample of CTCs (e.g., about 10 CTCs) requires the screening of $10^{10}$ cells or approximately 2 mL of blood. Ideally the entire analysis should take less than an hour. Thus, the sorter must operate at a throughput of approximately 1 µL's, corresponding to $5 \times 10^6$ cells/s. This is several orders of magnitude greater than the maximum throughput achievable using FACS. Other automated cell sorting systems are available, but these systems are typically slow, inefficient, expensive, or subject to contamination.

Therefore, in performing cell analysis, it would be desirable in many applications to have the ability to extract (i.e., sort, capture, and collect) single cells in an automated and high-throughput manner that overcomes the aforementioned and other disadvantages of the prior art.

SUMMARY OF THE INVENTION

One aspect of the present invention is a microfluidic device for extracting target objects from a sample. The microfluidic device comprises an aliquotting segment and a trapping segment. The aliquotting segment comprises a sample inlet channel, a first buffer inlet channel, a sample waste channel, and an aliquot delivery channel fluidly coupled at a fluid junction. The sample inlet channel and first buffer inlet channel are in fluid communication with an inlet end of the fluid junction and the sample waste channel and aliquot delivery channel are in fluid communication with an outlet end of the fluid junction. The aliquotting segment further comprises a second buffer inlet channel and a normally open valve, the second buffer inlet channel coupled to the fluid junction between the sample inlet channel and the sample waste channel, and the normally open valve operably coupled to the second buffer inlet channel.

Another aspect of the present invention is a system for extracting target objects from a sample. The system comprises a microfluidic device comprising an aliquotting segment in fluid communication with a trapping segment, the aliquotting segment comprising a normally open valve. The system further comprises an actuator operably coupled to the normally open valve, a detector in sensory communication with the microfluidic device, a processor operably coupled to the detector, and an electrode external to the microfluidic device and not bonded to the microfluidic device.

Yet another aspect of the present invention is a method for extracting target objects from a sample. In the method, a microfluidic device is provided, the microfluidic device comprising an aliquotting segment. The aliquotting segment comprises a sample inlet channel, a first buffer inlet channel, a sample waste channel, and an aliquot delivery channel fluidly coupled at a fluid junction. The aliquotting segment further comprising a second buffer inlet channel and a normally open valve, the second buffer inlet channel coupled to the fluid junction between the sample inlet channel and the sample waste channel, and the normally open valve operably coupled to the second buffer inlet channel. A first stream of buffer is directed through the first buffer inlet channel into the fluid junction and through the fluid junction into both the aliquot delivery channel and the sample waste channel. A second stream of buffer is directed through the second buffer inlet channel into the fluid junction and through the fluid junction into the sample waste channel. A stream of sample containing a plurality of target and non-target objects is directed through the sample inlet channel into the fluid junction and through the fluid junction into the sample waste channel, the first and second streams of buffer directing the stream of sample through the fluid junction and into the sample waste channel. A signal is detected from a target object flowing through a detection region of the sample inlet channel. In response to detecting the signal, an actuator is energized to close the normally open valve, resulting in a transient burst of crossflow out of the second buffer inlet channel and into the fluid junction, thereby directing an aliquot of sample into the aliquot delivery channel. Flowing the aliquot of sample through the aliquot delivery channel.

The aforementioned and other features and advantages of the invention will become further apparent from the following detailed description of the presently preferred embodiments, read in conjunction with the accompanying drawings, which are not to scale. In the drawings, like reference numbers indicate identical or functionally similar elements. The detailed description and drawings are merely illustrative of the invention, rather than limiting, the scope of the invention being defined by the appended claims and equivalents thereof.

BRIEF DESCRIPTIONS OF THE DRAWINGS

FIGS. 2A-2C are schematic illustrations of one embodiment of a normally open valve, in accordance with the present invention;

FIGS. 3A and 3B are schematic illustrations of another embodiment of a normally open valve, in accordance with the present invention;

FIGS. 7A-7D illustrate the removal of an individual object from the trapping segment of FIGS. 6A-6D using an electrode that is external to the microfluidic device and not bonded to the device, in accordance with the present invention.

DETAILED DESCRIPTION OF THE PRESENTLY PREFERRED EMBODIMENTS

One aspect of the present invention is a microfluidic device for extracting target objects (e.g., rare cells or molecules) from a sample. One embodiment of a microfluidic device in accordance with the present invention can be seen in FIG. 1. As illustrated, the microfluidic device includes an aliquotting segment 110 in fluid communication with a trapping segment 120.

Figure 1:
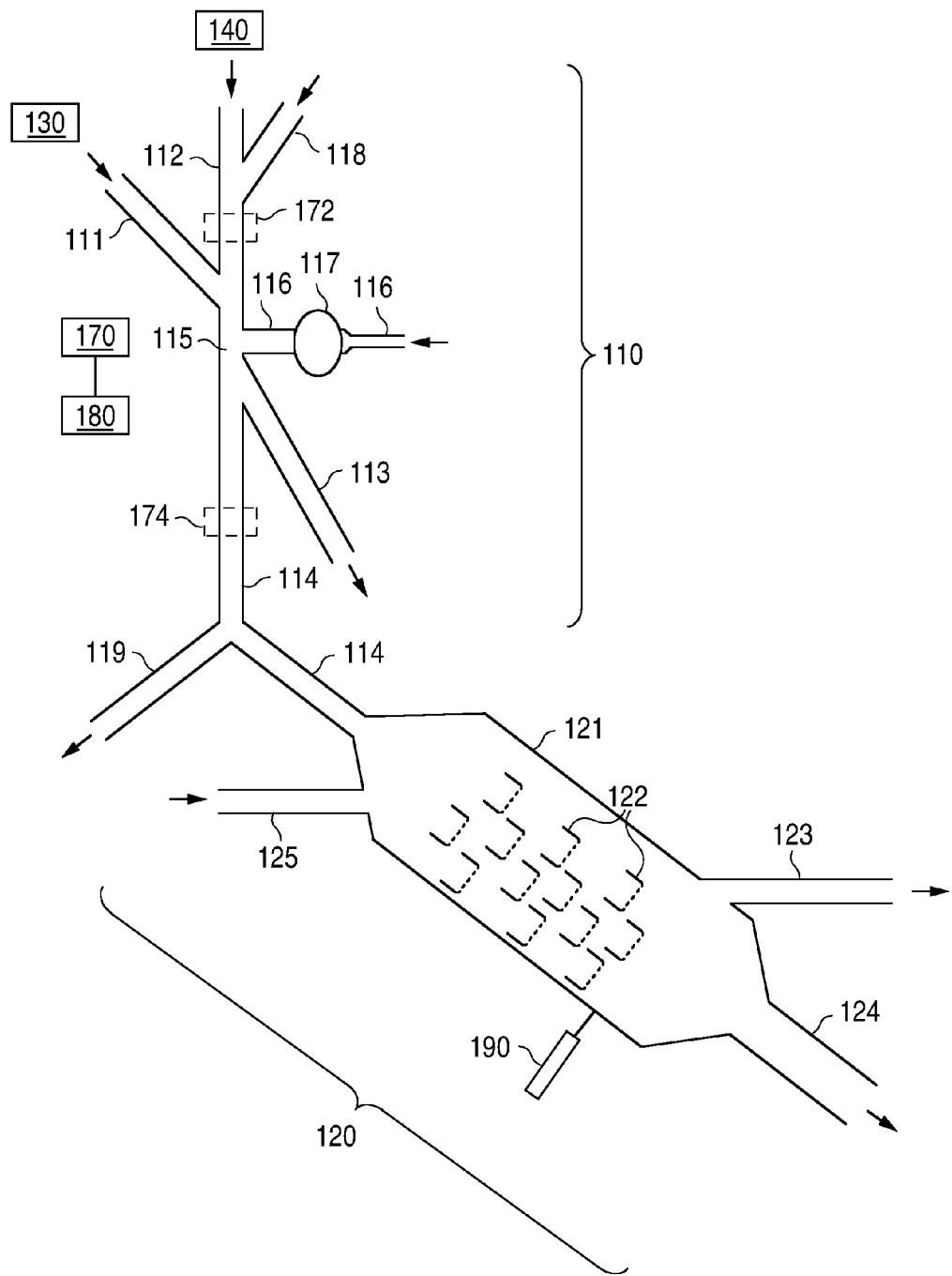
FIG. 1 is a schematic illustration of one embodiment of a system for extracting target objects from a sample, in accordance with the present invention.

Aliquotting segment 110 comprises a first buffer inlet channel 111, a sample inlet channel 112, a sample waste channel 113, and an aliquot delivery channel 114, all of which are fluidly coupled at a fluid junction 115. As can be seen in FIG. 1, channels 111 and 112 are in fluid communication with an inlet end of fluid junction 115, while channels 113 and 114 are in fluid communication with an outlet end of fluid junction 115.

Aliquotting segment 110 further comprises a second buffer inlet channel 116 coupled to fluid junction 115 between sample inlet channel 112 and sample waste channel 113. A normally open valve 117 is operably coupled to second buffer inlet channel 116. As illustrated in FIG. 1, aliquotting segment 110 also includes an optional third buffer inlet channel 118 coupled to first buffer inlet channel 112 upstream of second buffer inlet channel 116, plus an optional aliquot disposal channel 119 coupled to aliquot delivery channel 114 at a point downstream of fluid junction 115.

In the present embodiment, buffer inlet channels 111, 116, and 118 are in fluid communication with a buffer source 130. The term "buffer" is used herein to refer not only to buffering agents, but also to other fluids that are nonreactive with a sample from which target objects are to be extracted and so may be used in association with the sample.

Sample inlet channel 112 is in fluid communication with a sample source 140. The sample is typically a blood sample but may, alternatively, be any fluid sample from which a target object may be extracted, including not only aqueous phase fluid samples, but also samples comprising oils or other fluids. For example, the sample could be an emulsion of droplets in a carrier fluid (e.g., water in oil or oil in water) with the buffer streams consisting of pure carrier fluid.

One or both of buffer source 130 and sample source 140 may be a well or reservoir that is disposed in or on the microfluidic device and that contains a quantity of the appropriate material. Alternatively, one or both of the sources may be external to the microfluidic device and in fluid communication with the appropriate channel via a flexible tube, a rigid tube, a capillary, a cannula, or another tubular member that extends out from the microfluidic device.

The device is configured such that during a steady state, buffer flowing through inlet channels 111 and 116 directs sample flow through fluid junction 115 and into sample waste channel 113. It should be noted that the sample waste could be collected or directed into another area of the microfluidic device for further processing; i.e., the sample waste from the aliquotting segment is not necessarily discarded. When included, optional buffer inlet channel 118 delivers buffer into sample inlet channel 112, the two separate flows of buffer from inlet channels 111 and 118 acting in concert to focus the sample flow away from both side walls of channel 112.

Aliquot delivery channel 114 delivers sample aliquots into trapping segment 120, thereby providing fluid communication between aliquotting segment 110 and trapping segment 120. Optional aliquot disposal channel 119, which is coupled to aliquot delivery channel 114, can be included to permit disposal of a sample aliquot prior to its entry into trapping segment 120. Disposal may be desired, for example, if the aliquot is not confirmed to include a target object.

A normally open valve 117 is operably coupled to third inlet channel 116. The term "normally open valve" is used herein to refer to a valve that is open until an actuator is energized to close it. Normally open valves in accordance with the present invention are illustrated in FIGS. 2A, 2B, 3A, and 3B, which show side views of two embodiments of a normally open valve, and in FIG. 2C, which provides a top view of the valve of FIGS. 2A and 2B. As illustrated, the valve comprises a valve structure formed in the second buffer inlet channel and a deformable material disposed over at least a portion of the second buffer inlet channel in the area of the valve structure. The deformable material is sealed over the second buffer inlet channel portion except in the area of the valve structure, thereby forming a covered second buffer inlet channel portion that permits fluid to flow over the valve structure. The valve remains open until an actuator is energized to press the deformable material onto the valve structure, thereby closing the valve.

One embodiment of the normally open valve can be seen in FIGS. 2A-2C. As illustrated in these figures, a microfluidic device in accordance with the present invention comprises at least a channel layer 252 and a cover layer 254 (seen also at 852 and 854, respectively, in FIG. 8). In the present embodiment, the channels of the aliquotting segment are formed in channel layer 252, while cover layer 254 is a thin sheet or film that covers the channels.

Channel layer 252 and cover layer 254 are sealed together over second buffer inlet channel 216 except in an area 217a of cover layer 254 where the two layers are delaminated (i.e., not sealed together and capable of separation). Area 217a can be seen as an oval in the center of FIG. 2C. As illustrated in the figures, cover layer area 217a is positioned over a valve structure 217b that is formed across the entire width of channel 216, forming a discontinuity in channel 216.

At least the delaminated (unsealed) area 217a of cover layer 254 is constructed of a material capable of being deformed away from valve structure 217b to permit buffer to flow over valve structure 217b as seen in FIG. 2A. I.e., area 217a is shaped so as to form a dome to allow fluid to flow over valve structure 217b.

FIG. 2A illustrates the normally open status of valve 217. FIG. 2B shows valve 217 in a closed status, an actuator 260 having been energized to impact area 217a, pressing area 217a of cover layer 254 onto valve structure 217b, thereby preventing buffer from flowing over valve structure 217b and further into channel 216. Note that it is not necessary for the flow of buffer over valve structure 217b to be entirely blocked. As described in more detail below, it is the act of closing the valve, resulting in the buffer within the valve (i.e., the buffer flowing over the valve structure beneath the domed area 217a) being ejected out of the valve as a burst of flow, that is a necessary element of the invention.

In another embodiment, illustrated in FIGS. 3A and 3B, the microfluidic device comprises two substrates 352 and 356 that are bonded together to form the microfluidic device. The channels of aliquotting segment 110 are formed in at least one of the two substrates, that substrate identified as channel layer 352 in FIGS. 3A and 3B. The other substrate serves as a cover layer and is seen at 356 in FIGS. 3A and 3B.

In this embodiment, substrate 356 includes at least one aperture 358. This aperture is positioned over a valve structure 317b that is disposed across the entire width of inlet channel 316 and forms a discontinuity in channel 316. Both channel 316 and valve structure 317b are formed in channel layer 352. A material capable of deforming is trapped between substrates 352 and 356 in the area of aperture 358, this material forming a deformable area 317a over valve structure 317b that is shaped so as to form a dome, allowing fluid to flow over valve structure 317b beneath the dome.

As illustrated in FIG. 3A, area 317a is deformed into aperture 358 to permit buffer to flow over valve structure 317b. FIG. 3A illustrates the normally open status of valve 317, while FIG. 3B shows valve 317 in a closed status, an actuator 360 having been energized to travel into aperture 356 to press deformable area 317a onto valve structure 317b, thereby preventing buffer from flowing over valve structure 317b. Note that it is not necessary for the flow of buffer over valve structure 317b to be entirely blocked. As described in more detail below, it is the act of closing the valve, resulting in the buffer within the valve (i.e., the buffer flowing over the valve structure beneath the domed area 317a) being ejected out of the valve as a burst of flow, that is a necessary element of the invention.

Figure 9A:
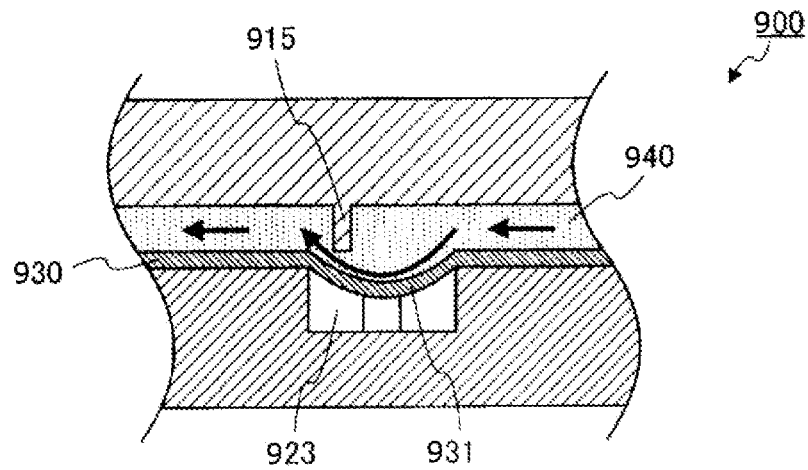
FIGS. 9A and 9B are schematic illustrations of another embodiment of a normally open valve, in accordance with the present invention.
Figure 9B:
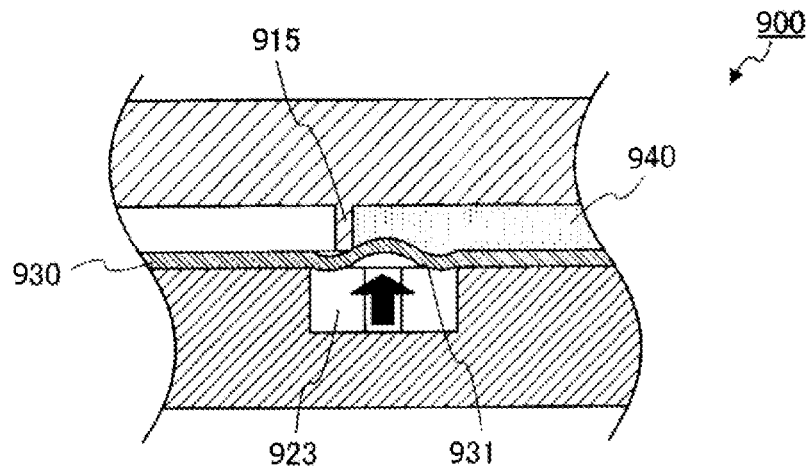

In another embodiment, illustrated in FIGS. 9A and 9B, the normally open valve includes a fluid actuated diaphragm. An exemplary normally open valve is described in WIPO Publication Number WO/2013/014905, published Jan. 31, 2013, entitled Fluid Treatment Apparatus and Method for Treating Fluid (International Application Number PCT/JP2012/004651). Microfluidic device 900 includes a normally open valve comprising diaphragm 931 of film 930, septum 915, and pressure chamber 923. As illustrated in FIG. 9A, liquid 940 flows between septum 915 and diaphragm 931 when pressure chamber 923 is depressurized. As illustrated in FIG. 9B, the flow of liquid 940 is stopped when pressure chamber 923 is pressurized to force diaphragm 931 against septum 915.

Other normally open valves may be used provided the valve when open and in operation contains a quantity of buffer that is ejected from the valve when the valve is closed rapidly by an actuator. Such closure results in a transient burst of cross-flow out of second buffer inlet channel 116 and into fluid junction 115, as described in more detail below. The valve is preferably capable of being opened and closed in less than 1 ms.

Returning now to FIG. 1, aliquotting segment 110 can be seen to be in fluid communication with trapping segment 120 via aliquot delivery channel 114. Trapping segment 120 comprises a trapping chamber 121 and a plurality of trapping structures 122 disposed in chamber 121. Trapping segment 120 also comprises a collection channel 123 and a waste channel 124 in fluid communication with chamber 121. Collection channel 123 is used in extracting individual target objects from chamber 121. Waste channel 124 is used to carry unwanted objects and waste fluids out of the trapping chamber.

Trapping segment 120 may include one or more additional channels in fluid communication with chamber 121, one of which can be seen at 125. The additional channel(s) can be used to expose objects trapped within chamber 121 to various fluids. For example, the additional channel(s) may be used to introduce reagents for analysis or processing of trapped objects and/or to introduce oil into chamber 121 in order to form aqueous droplets around individual objects (as described below).

Figure 4A:
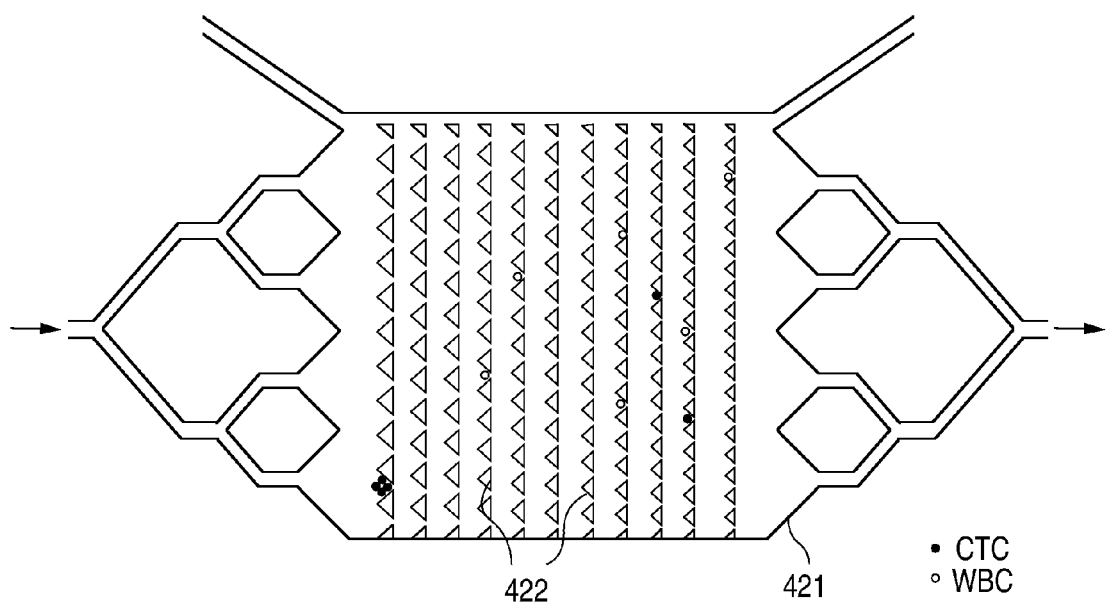
FIG. 4A is a schematic illustration of an alternative embodiment of a trapping chamber, in accordance with the present invention.
Figure 4B:
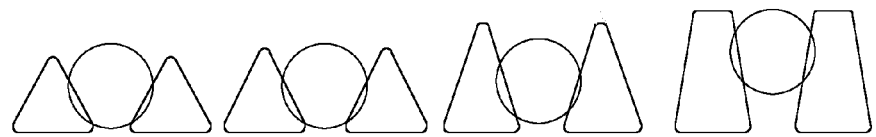
FIG. 4B is a schematic illustration of alternative embodiments of trapping structures, in accordance with the present invention.

Both chamber 121 and trapping structures 122 may be any shape or size suitable for trapping the intended target objects. FIGS. 1 and 6A-7D show a simplified and stylized chamber. This is done for simplicity in FIG. 1 and for clarity of illustrating the trapping and subsequent transporting of objects in FIGS. 6A-7D. FIG. 4A illustrates a more detailed chamber 421, and FIG. 4B illustrates possible trapping structures. In FIG. 1, trapping structures 122 are all the same size, trapping target objects while allowing smaller objects to pass between and/or through the structures and into waste channel 124 (as seen, for example, in FIG. 6D). In FIG. 4, the plurality of trapping structures 422 are arranged in an array that is constructed such that larger objects and clusters of objects are trapped nearer to the entrance of the array, with progressively smaller objects trapped further into the array. Individual trapping structures may be designed such that when the trapping chamber is flushed with oil, trapped objects will be encapsulated in an aqueous droplet, one trapped object per droplet. This can be aided by constructing the trapping structures of a material that is hydrophobic.

Where objects are to be removed from the chamber following trapping, a passage is provided within the trapping chamber (e.g., formed by an absence of trapping structures in an area of the chamber) to permit trapped objects to be manipulated through this passage. See, for example, the passage formed in the area adjacent to the side of chamber 121 that is in fluid communication with collection channel 123. FIG. 7C shows a circulating tumor cell (CTC) being manipulated through this channel.

The area of the microfluidic device within which the trapping chamber is disposed is preferably optically transparent through either a top or bottom surface of the device to permit imaging of objects trapped within the chamber. I.e., either the cover layer or the channel layer of the microfluidic device is optically transparent in at least the area of the microfluidic device within which the trapping chamber is disposed, resulting in an external wall of the trapping chamber being optically transparent.

To permit dielectrophoretic (DEP) manipulation of trapped objects (as described in more detail below), at least an external wall of chamber 121 comprises a material that is penetrable by an electric field generated external to the device, the electric field thereby capable of extending through the material and into the chamber. The penetrable wall may be formed, for example, from a thin polymer film (preferably ≤100 microns thick) or an anisotropically conductive layer that is conductive only in the direction through the thickness of the layer (preferably ≤5 mm).

Dielectrophoretic and other manipulation techniques may be used to move an object (or an object encased in an aqueous droplet) into other regions of the microfluidic device for removal from the device or for further manipulation and analysis on or within the microfluidic device. For example, collection channel 123 may be in fluid communication with a well disposed on a surface of the microfluidic device from which a target object may be withdrawn for further processing or within which the object may be further analyzed. Alternatively, collection channel 123 may be in fluid communication with (or may itself comprise) a tubular member such as a flexible tube, a rigid tube, a capillary, or a cannula that extends out from the microfluidic device to deposit a target object onto a slide or into a multiwell plate. In yet another alternative, the microfluidic device may include channels and/or chambers that serve as analysis modules for analytical techniques such as polymerase chain reaction (PCR), fluorescence in situ hybridization (FISH), and immunochemistry.

Figure 8:
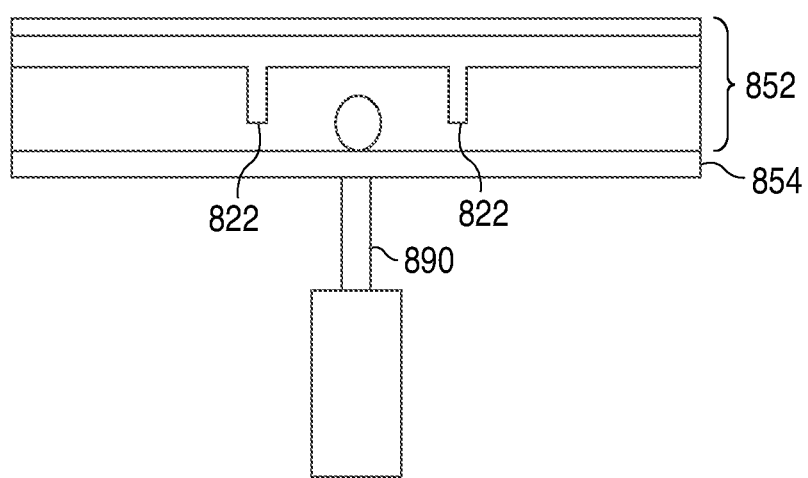
FIG. 8 illustrates an external electrode positioned adjacent to a penetrable wall of a trapping segment, in accordance with the present invention.

As previously mentioned, a microfluidic device according to the present invention comprises at least a channel layer and a cover layer. The channel layer may be a single substrate (as seen in FIG. 2A) or may comprise multiple substrates assembled to form the channel layer (as seen in FIG. 8). Suitable materials for the channel layer include elastomers and polymers such as polydimethylsiloxane (PDMS), polymethylmethacrylate (PMMA), polycarbonate, polytetrafluoroethylene (PTFE), polyvinylchloride (PVC), polysulfone, polystyrene, polymethylpentene, polypropylene, polyethylene, polyvinylidine fluoride, ABS (acrylonitrile-butadiene-styrene copolymer), cyclic-olefin polymer (COP), and cyclic-olefin copolymer (COC). Other suitable materials include glass, quartz, and silicon. The thickness of the channel layer is dependent on the depth of the channels and chamber(s) to be formed in the layer and other factors such as the instrument with which the device will be used. Most of the materials named above are or can be made optically transparent to permit imaging of trapped objects within the trapping chamber.

The channels, valve structure, chamber, and trapping structures may be formed in the channel layer by a variety of methods known in the art, including photolithography, machining, molding, wet chemical etching, reactive ion etching (RIE), laser ablation, air abrasion techniques, injection molding, LIGA methods, metal electroforming, embossing, and combinations thereof. Surface properties of the channel are important, and techniques are known in the art to either chemically treat or coat the channel surfaces so that those surfaces have the desired properties. For example, glass can be treated (e.g., covered with PDMS or exposed to a perfluorinated silane) to produce channel walls that are hydrophobic and therefore compatible with a fluorocarbon oil. In the case of semiconductive materials such as silicon, an insulating coating or layer (e.g., silicon oxide) can be provided over the channel layer material.

Suitable materials for the cover layer include the elastomers and polymers named above for the channel layer as well as glass, quartz, and silicon in areas that are not required to be deformable. The entire cover layer may be made of a single material that is deformable (accommodating the normally open valve) as well as optically transparent and suitable for dielectrophoretic manipulation of a trapped object (accommodating the trapping chamber). For example, a single-material cover layer may be a plastic or anisotropically conducting film. Both plastic and anisotropically conducting films are commercially available, with various anisotropically conductive films being offered by the 3M company, for example. Alternatively, the cover layer may comprise different materials covering different areas of the channel layer, with glass being an acceptable material except in the valve area, which is required to be deformable. In yet another alternative, the microfluidic device may comprise more than one cover layer as described below.

The cover layer is affixed to the channel layer (except in the area of the microfluidic device within which the normally open valve is disposed) by any appropriate method known in the art, those methods including chemical bonding, thermal bonding, adhesive bonding, and pressure sealing. For example, a thin polymer or anisotropically conducting film or sheet can be bonded to a channel layer using thermal or adhesive bonding or pressure sealing, with heat, an adhesive, or pressure being withheld in the area of the normally open valve (e.g., in the area seen at 217a in FIGS. 2A-2D).

Other combinations of cover and channel layers are possible. For example, a microfluidic device according to the present invention may comprise two cover layers and either a single-substrate channel layer or a multiple-substrate channel layer. In one example, one or more of the channels and the valve structure are fabricated into one substantially planar surface of a single-substrate channel layer, while the trapping chamber is fabricated into the other substantially planar surface of the single substrate. The trapping chamber is in fluid communication with the elements fabricated on the other surface of the substrate by means of one or more vias through the thickness of the substrate. Alternatively, the trapping chamber may be fabricated into a first substrate and the channel(s) and valve structure fabricated into a second substrate. The fabricated elements are then in fluid communication through the two (or more) substrates by means of one or more vias.

The single- or multiple-substrate channel layer may then have a different cover layer disposed over the two surfaces of the channel layer. In this embodiment, a film suited to the deformable valve portion may be disposed on the surface of the channel layer that includes the valve structure, while a film that is both optically transparent and suitable for dielectrophoretic manipulation of a trapped object may be disposed on the surface of the channel layer that includes the trapping chamber. This construction relieves the constraint that a single cover layer be deformable, optically transparent, and suitable for dielectrophoretic manipulation of a trapped object.

The microfluidic device described above may be combined with additional elements to form a system. Thus, another aspect of the present invention is a system for extracting target objects from a sample, the system comprising a microfluidic device including a normally open valve, an actuator operably coupled to the normally open valve, a detector in sensory communication with the microfluidic device, a processor operably coupled to the detector, and an electrode external to the microfluidic device and not bonded to the device. One embodiment of the system is illustrated in FIG. 1.

The microfluidic device is as described above and illustrated in the figures, comprising an aliquotting segment 110 and a trapping segment 120. Aliquotting segment 110 comprises a first buffer inlet channel 111, a sample inlet channel 112, a sample waste channel 113, and an aliquot delivery channel 114, all of which are fluidly coupled at a fluid junction 115. Channels 111 and 112 are in fluid communication with an inlet end of fluid junction 115, while channels 113 and 114 are in fluid communication with an outlet end of fluid junction 115. Aliquotting segment 110 further comprises a second buffer inlet channel 116 coupled to fluid junction 115 between sample inlet channel 112 and sample waste channel 113. A normally open valve 117 is operably coupled to second buffer inlet channel 116. Valve 117 is as described above and illustrated in FIGS. 2A, 2B, 2C, 3A, and 3B. The aliquotting segment may additionally comprise an optional third buffer inlet channel 118 that is coupled to first buffer inlet channel 112 upstream of second buffer inlet channel 116 and an optional aliquot disposal channel 119 that is coupled to aliquot delivery channel 114 at a point downstream of fluid junction 115.

Trapping segment 120 comprises a trapping chamber 121 that is fluidly coupled with aliquot delivery channel 114. An array of trapping structures 122 is disposed in chamber 121, and both a collection channel 123 and a waste channel 124 are in fluid communication with chamber 121. Collection channel 123 is used in extracting individual target objects from chamber 121. Waste channel 124 is used to carry unwanted objects and waste fluids out of chamber 121. Trapping segment 120 may include one or more additional channels in fluid communication with chamber 121, one of which can be seen at 125. The additional channel(s) can be used to expose objects trapped within chamber 121 to various fluids such as reagents and/or oil.

An actuator according to the present invention is illustrated at 260 and 360 in FIGS. 2A, 2B, 3A, and 3B. The actuator is preferably a high-speed mechanical actuator, e.g., an ultrasonic piezo actuator, with sufficient force and speed to close a normally open valve in less than 1 msec. Such actuators are commercially available. For example, Physik Instrumente GmbH & Co. sells precision actuators for micro-positioning that have speeds of 350 µm/ms and maximum force of 6 N. This force corresponds to a pressure on the delaminated or unsealed area (217a or 317a) of the normally open valve of more than 10,000 PSI, which is well beyond the pressure necessary for present purposes.

The system comprises a detector 170 positioned in sensory communication with the microfluidic device, as seen in FIG. 1. As used herein, the phrase "in sensory communication" refers to positioning of a detector such that it is operably connected to the device, i.e., capable of receiving a detectable signal from the contents of the device. In the case of optical signals, this requires only that the detector be positioned to receive the optical signal. Detector 170 may employ laser-induced fluorescence to detect single target objects and is preferably capable of detecting a single object (e.g., a cell) in a background of 10,000 objects moving at 10 cm/s.

As can be seen in FIG. 1, detector 170 is positioned such that it is in sensory communication with a detection region 172 of sample inlet channel 112. As described above, channel 112 carries a fluid sample such as blood. Detection of a target object within detection region 172 triggers creation of an aliquot of sample that contains the target object as explained below.

Detector 170 may also be in sensory communication with a second detection region 174, located in aliquot delivery channel 114. Detection of a target object within detection region 174 verifies that a target object was successfully directed into aliquot delivery channel 114 in a sample aliquot. If detector 170 fails to detect a signal within detection region 174, the aliquot then present within region 174 may be directed into aliquot disposal channel 119, which is coupled to channel 114 and serves as a waste channel.

A processor, seen at 180 in FIG. 1, is operably coupled to detector 170 and receives data collected using the detector. Processor 180 is configured to perform real-time analyses of the collected data and may be any processor capable of analyzing the data to distinguish target from non-target objects. The processor includes instructions for identifying specific target objects; e.g., a non-transitory computer readable medium is coupled to the processor that stores a computer program that includes information regarding the distinguishing features of the target objects. The processor is also capable of translating the results of the analysis into a signal that energizes the actuator to close the normally open valve.

The external electrode, shown at 190 in FIG. 1 and at 890 in FIG. 8, is used to manipulate objects within the trapping segment of the microfluidic device. Objects to be manipulated include, for example, cells, droplets, particles, molecules, and combinations thereof. The act of manipulating the object(s) includes immobilizing the object(s), releasing the object(s), moving the object(s), merging the object with another object (e.g., merging a cell with a droplet), and combinations thereof.

As seen in FIGS. 1 and 8, the electrode is a single electrode such as, for example, a single needle electrode, a single metal pad on a PCB, or another electrode such as is known in the art. However, the electrode may also be one of an array of electrodes. The array may be, for example, multiple metal pads on a printed circuit board (PCB) or multiple needle electrodes (i.e., substantially needle-shaped conductors of electric current) held together by a fixture. The electrode or electrode array can be an independent device or a constituent of an instrument that is configured to interact with the microfluidic device.

When the system is in operation, the electrode or electrode array is positioned adjacent to an external surface of the microfluidic device in the area of the trapping chamber (seen, e.g., in FIG. 1 at 121). I.e., the electrode or electrode array is positioned such that it is either in physical contact with or in proximity to the external surface of a top or bottom wall of the trapping chamber. "In proximity to" is defined herein as being within 100 microns of the external surface of the chamber wall. The electrode or electrode array is preferably within 10 microns of or in contact with the external surface of the chamber wall. The electrode or electrode array is not bonded to the microfluidic device and is translatable across the external surface of the chamber wall. I.e., the electrode or electrode array is movable in the plane of the chamber wall such that the electrode or electrode array moves across the external surface of the chamber wall. This may be accomplished either by moving the electrode or electrode array or by moving the microfluidic device. The electrode or electrode array generates an electric field using either alternating current (AC) or direct current (DC).

Yet another aspect of the present invention is a method for extracting target objects from a sample. The method may be performed using a system such as has been described above, taking advantage of the unique features of the system. One embodiment of the method is illustrated in FIGS. 5A-7D.

A microfluidic device is provided in the method. The device includes an aliquotting segment such as is illustrated in FIG. 1 at 110 and also in FIGS. 5A-5D. The aliquotting segment comprises a sample inlet channel, a first buffer inlet channel, a sample waste channel, and an aliquot delivery channel, all of which are fluidly coupled at a fluid junction. The sample inlet channel and the first buffer inlet channel are in fluid communication with an inlet end of the fluid junction, while the sample waste channel and aliquot delivery channel are in fluid communication with an outlet end of the fluid junction. The aliquotting segment further comprises a second buffer inlet channel coupled to the fluid junction between the sample inlet channel and the sample waste channel. A normally open valve is operably coupled to the second buffer inlet channel.

Figure 5A:
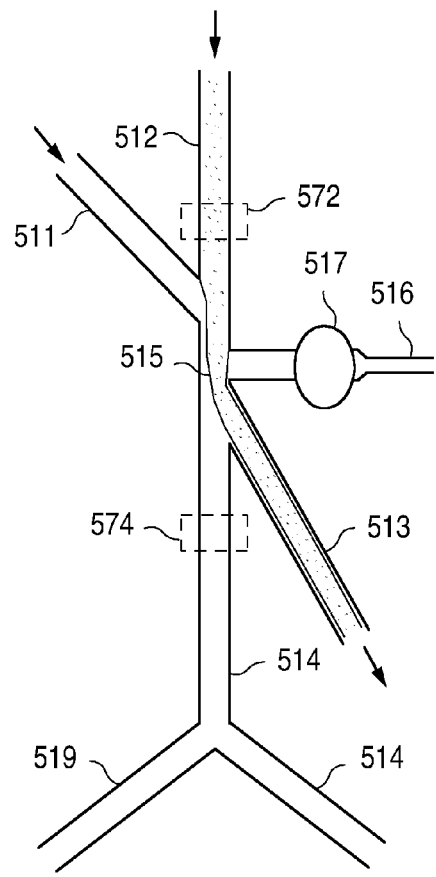
FIGS. 5A-5D illustrate the operation of an aliquotting segment of a microfluidic device, in accordance with the present invention.

As can be seen in FIG. 5A, a first stream of buffer is directed through first buffer inlet channel 511 into fluid junction 515 and through fluid junction 515 into both aliquot delivery channel 514 and sample waste channel 513. A second stream of buffer is directed through second buffer inlet channel 516 into fluid junction 515 and through fluid junction 515 into sample waste channel 513. A stream of sample containing a plurality of target and non-target objects is directed through sample inlet channel 512 into fluid junction 515 and through fluid junction 515 into sample waste channel 513. In the steady state seen in FIG. 5A, the flow of buffer through channels 511 and 516 directs sample flow through fluid junction 515 and into sample waste channel 513. Buffer may also be flowed into first buffer inlet channel 512 from an optional third buffer inlet channel such as the one seen at 118 in FIG. 1 to focus the flow of sample within channel 512.

An optical (or other) signal is detected from a target object flowing through detection region 572 of sample inlet channel 512. The sample may be first mixed with fluorescent antibodies or other markers. In some applications it may be advantageous to use a probe that is shifted into the red, where the autofluorescence of blood is minimal. For example, Cy5 has an excitation peak at 650 nm and an emission peak at 670 nm.

Figure 5B:
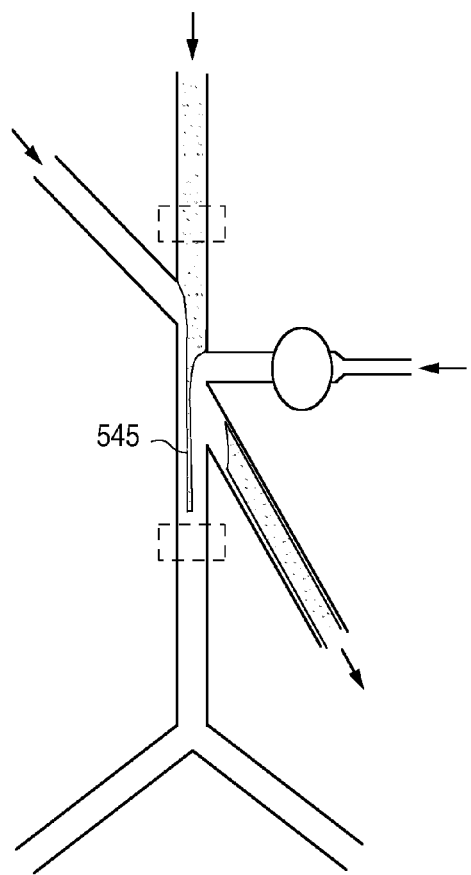

In response to detection of the signal, an actuator is energized to close the normally open valve 517 operably connected to second buffer inlet channel 516. Closure of the valve results in a transient burst of cross-flow out of second buffer inlet channel 516 and into fluid junction 515, thereby directing an aliquot of sample into aliquot delivery channel 514 as seen in FIG. 5B.

This result of closing the normally open valve is best understood by referring to FIGS. 2A and 3A and observing the buffer flowing over valve structures 217b and 317b. When the delaminated or unsealed area of the valve (217a or 317a) is rapidly and forcefully pressed onto the valve structure (217b or 317b) by an actuator, as seen in FIGS. 2B and 3B, the buffer within the valve (i.e., the buffer flowing over the valve structure beneath the delaminated or unsealed area) is ejected out of the valve as a burst of flow. As seen in FIG. 5B, this burst of flow is directed through third inlet channel 516 and into fluid junction 515 as a cross-flow within fluid junction 515, briefly diverting the flow of sample within the fluid junction and resulting in an aliquot of sample (seen at 545 in FIGS. 5B-5D) being directed into aliquot delivery channel 514. In the method it is desirable for approximately 1-nL aliquots to be diverted from a much larger volume (e.g., several milliliters) of sample. Throughput of the sample is preferably ≥1 µL/s.

Note that it is not necessary for the flow of buffer through valve 517 to be completely blocked by closure of the valve. As described above, it is the transient burst of cross-flow out of second buffer inlet channel 516 and into fluid junction 515 that deflects an aliquot of sample into aliquot delivery channel 514; a continued flow of buffer through valve 517 would not interfere with this action. Nonetheless, a complete absence of flow through valve 517 may be desired because an absence of flow may act to terminate deflection of the aliquot of sample more rapidly, resulting in a smaller volume aliquot. In addition, an absence of flow from second buffer inlet channel 516 into fluid junction 515 when valve 517 is completely closed allows flow from first buffer inlet channel 512 to more effectively direct unwanted sample into sample waste channel 513 following diversion of an aliquot into aliquot delivery channel 514.

Figure 5C:
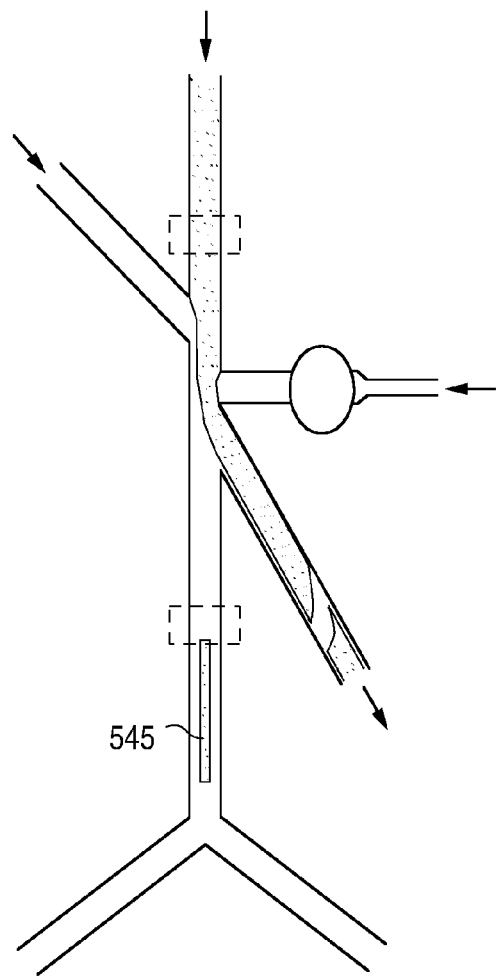

The diversion of the sample stream occurs only as the valve is closing, with the burst of cross-flow limited by the amount of buffer within the open valve at the time the valve closes. The valve is preferably capable of being opened and closed in less than 1 msec. The valve need not be reopened for the sample flow to revert to sample waste channel 513 as seen in FIG. 5C because the flow of buffer through channel 511 again directs the sample flow into channel 513 as soon as the burst of cross-flow ends. Thus, the combination of the valve and the actuator is essentially a self-limiting pulse generator. Valve 517 has been reopened in FIG. 5D, and the aliquotting segment is ready to divert a second aliquot of sample into channel 514.

Presence of the desired target object within the aliquot may be confirmed by again detecting an optical (or other) signal from the target object within a second detection region 574 positioned within channel 514. If no signal is detected, indicating that the target object was not successfully directed into channel 514 in the aliquot, the aliquot may be directed into waste channel 519.

Aliquots confirmed to contain at least one target object (and aliquots not subjected to confirmatory testing in the method) continue on through channel 514 toward a trapping segment such as is illustrated in FIG. 1 at 120 and also in FIGS. 6A-7D. As illustrated, the trapping segment comprises a chamber, an array of trapping structures disposed in the chamber, and both a collection channel and a waste channel in fluid communication with the trapping chamber. The trapping segment may also comprise a reagent delivery channel.

Figure 5D:
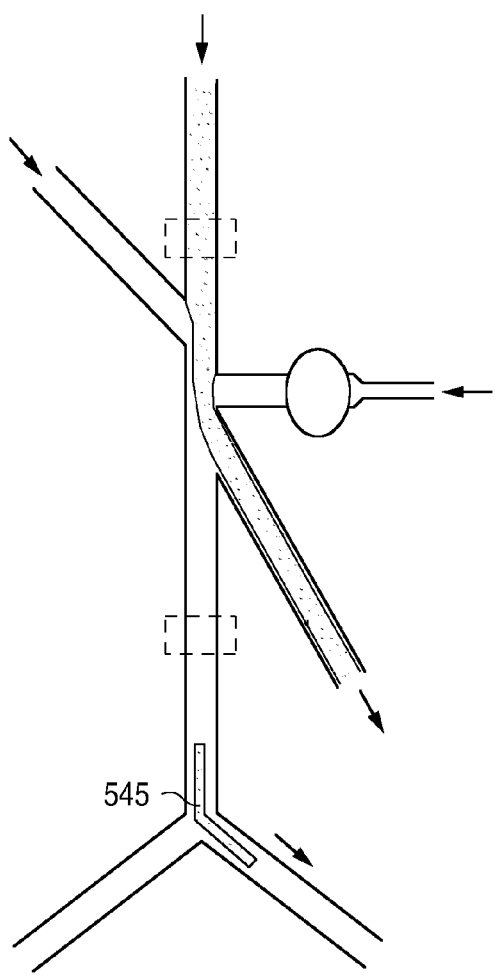
Figure 6A:
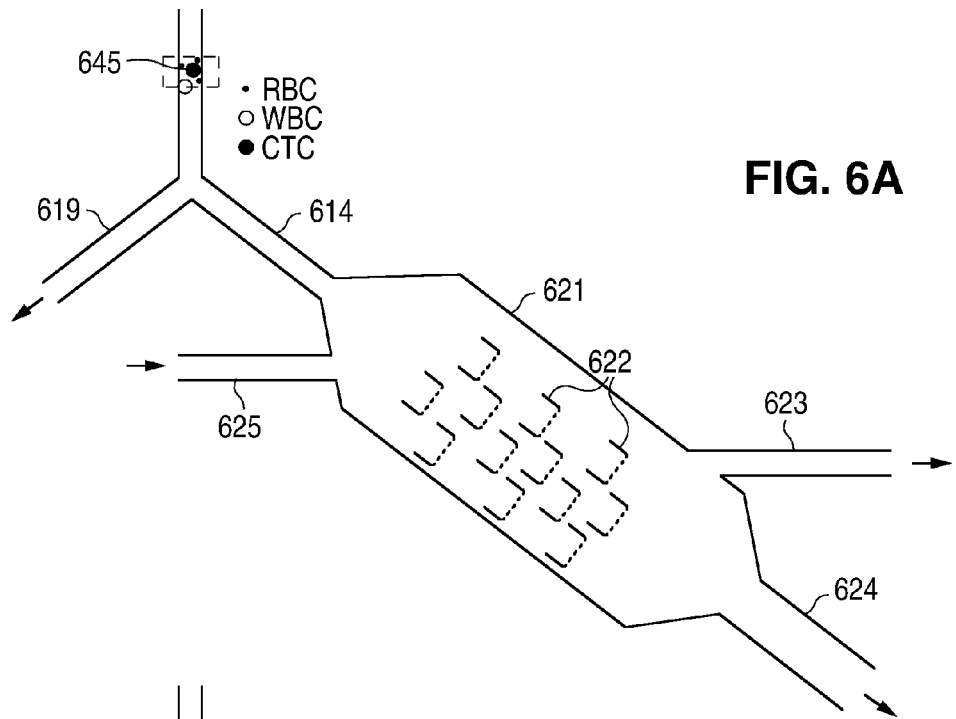
FIGS. 6A-6D illustrate the operation of a trapping segment of a microfluidic device, in accordance with the present invention.
Figure 6B:
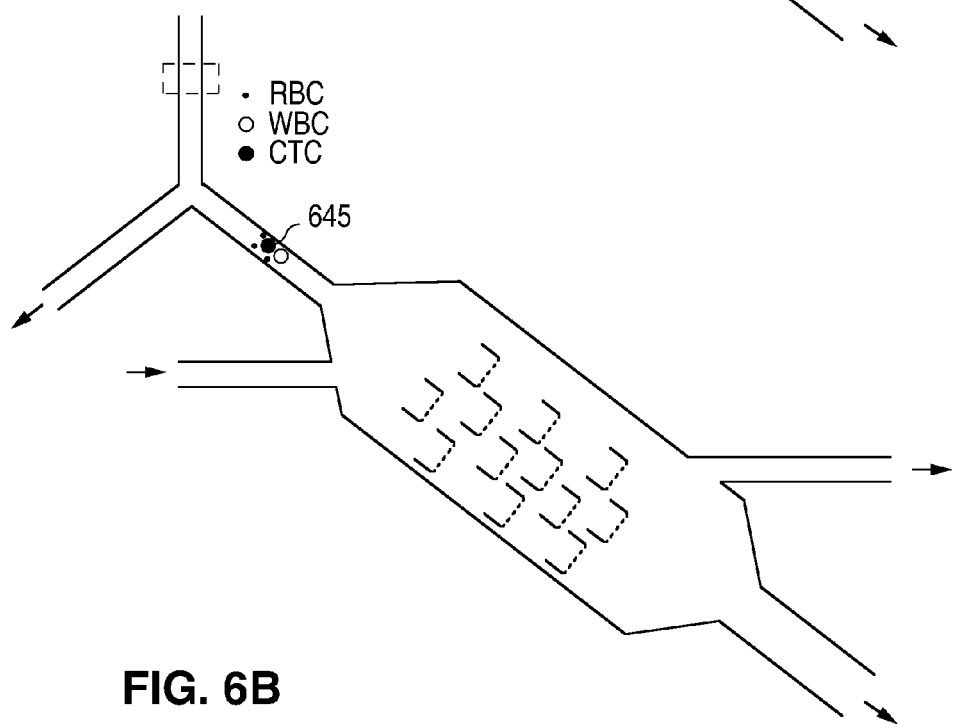
Figures 6C, 6D:
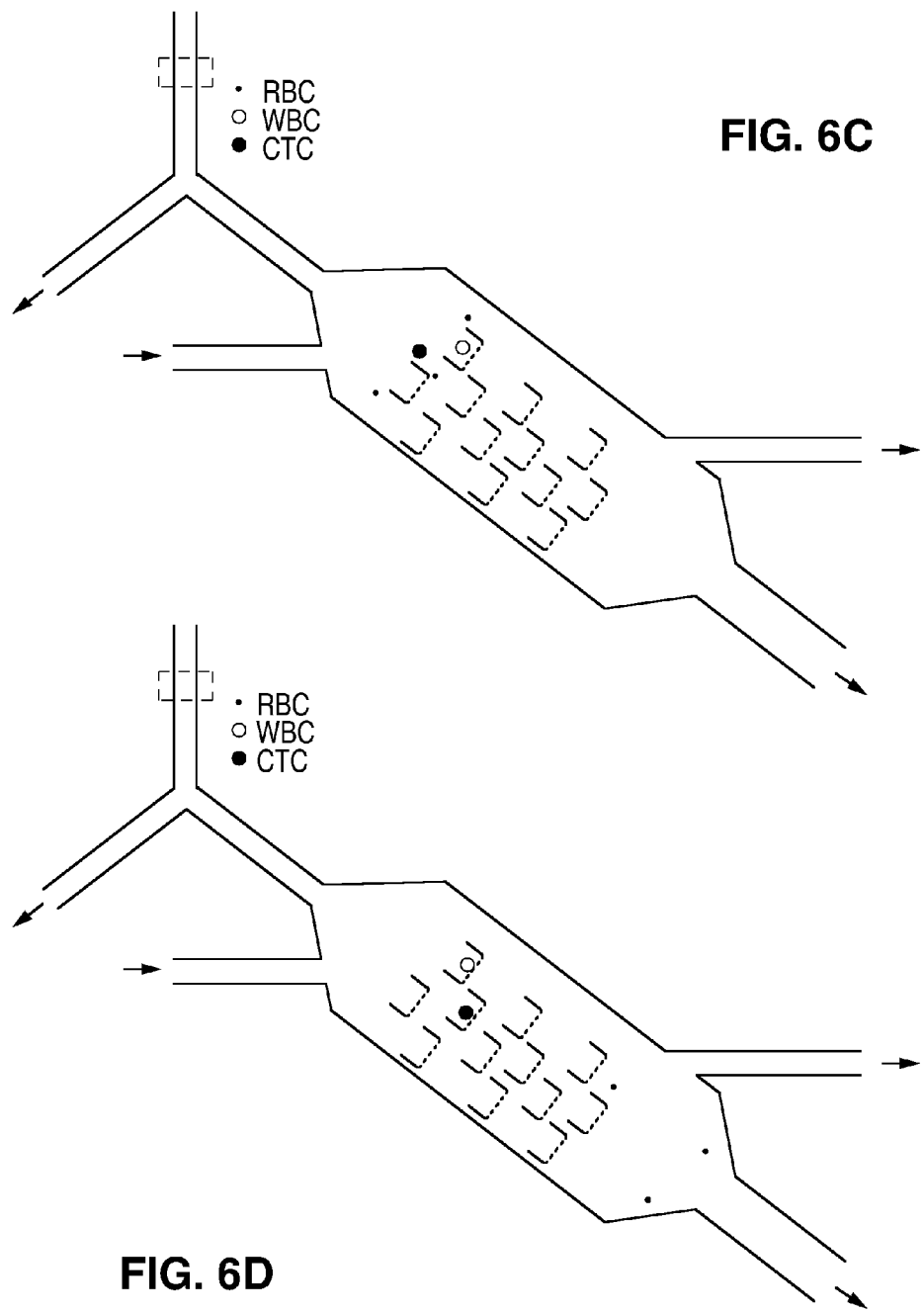

As seen in FIGS. 6A-6D, the aliquot of sample flows out of aliquot delivery channel 614 and into trapping chamber 621. For ease of illustrating movement of the individual target and non-target objects contained in an aliquot of sample, the aliquot seen at 545 in FIGS. 5B-5D is illustrated in FIGS. 6A and 6B as a cluster of individual cells 645. Once the aliquot enters the trapping chamber, as seen in FIGS. 6C and 6D, one or more target objects within the aliquot are trapped by trapping structures 622, and non-target objects pass out of the trapping chamber through waste channel 624. In the illustrated example, white blood cells (WBCs) and circulating tumor cells (CTCs) are trapped within chamber 621, while red blood cells (RBCs) pass out of the trapping chamber through waste channel 624.

Various operations may be performed on the objects while they are trapped within the chamber. For example, imaging reagents such as fluorescent molecular markers may be flowed into chamber 621 through channel 625, and multispectral (or other) imaging may be performed on the trapped objects in situ. As seen in FIG. 6D, a white blood cell (WBC) and a circulating tumor cell (CTC) are trapped within trapping chamber 621. Fluorescent molecular markers may be added via channel 625 to stain the cells and distinguish the circulating tumor cell, the target object in this example, from the white blood cell. Reagents for performing analytical techniques such as fluorescence in situ hybridization (FISH) and immunochemistry may also be flowed into chamber 621 through channel 625 and the appropriate analysis technique performed on the trapped objects.

A polymerase chain reaction (qPCR or digital PCR) may be performed on trapped cells in situ by first flushing the trapping chamber with PCR reagents and then with oil. Cells are typically hydrophilic, so when oil flows into the trapping chamber, the oil encloses both the individual cell and a droplet of liquid comprising the PCR reagents surrounding the cell. In this example, the trapping structures within the trapping chamber are preferably constructed of a material that is hydrophobic. Once a cell is enclosed within the oil droplet, the cell may be lysed, and PCR may be performed on the cell in situ within the trapping chamber.

Alternatively or additionally, an object (or an object enclosed within an oil droplet) may be manipulated using dielectrophoresis (DEP), electrophoresis, or other manipulation techniques to direct the object out of the trapping chamber for further processing. Where the object is to be manipulated using DEP, the object and a small quantity of buffer surrounding the object are preferably enclosed in oil to form a droplet.

In a DEP manipulation technique, the object can be manipulated by an electrode that is external to the microfluidic device and not bonded to the device. The electrode is translatable across an external surface of the trapping chamber wall (i.e., the electrode is movable in the plane of the wall such that the electrode moves across the external surface of the trapping chamber wall). This may be accomplished either by moving the electrode or electrode array or by moving the microfluidic device. When using DEP, the trapping chamber wall is made of a material that is penetrable by an electric field generated external to the device by the electrode, the electric field thereby extending through the wall and into a region within the trapping chamber.

In DEP, a force is exerted on a dielectric object when it is subjected to a non-uniform electric field. All objects exhibit some dielectrophoretic activity in the presence of an electric field regardless of whether the object is or is not charged. The object need only be polarizable. The electric field polarizes the object, and the resulting poles experience an attractive or repulsive force along the field lines, the direction depending on the orientation of the dipole. The direction of the force is dependent on field gradient rather than field direction, and so DEP occurs in alternating current (AC) as well as direct current (DC) electric fields. Because the field is non-uniform, the pole experiencing the greatest electric field will dominate over the other, and the object can be immobilized or moved and then released by the external electrode.

In the current method, the external electrode is placed adjacent to the penetrable wall of the trapping chamber as seen in FIG. 8. Placing the electrode adjacent to the wall includes both placing the electrode in physical contact with the penetrable wall and placing the electrode in proximity to (i.e., within 100 microns of and preferably within 10 microns of) the penetrable wall of the trapping chamber. The electrode is energized to generate an electric field. The electrode may be energized either before or after being placed adjacent to the penetrable wall; however, care should be taken to avoid attracting undesired droplets when the electrode is energized before being placed adjacent to the desired object. The penetrable wall of the trapping chamber is penetrated by the electric field such that the electric field extends through the wall and into a region within the chamber. An object within the chamber is then manipulated using DEP. For additional information, please see co-pending U.S. patent application Ser. No. 13/705,670.

Figure 7A:
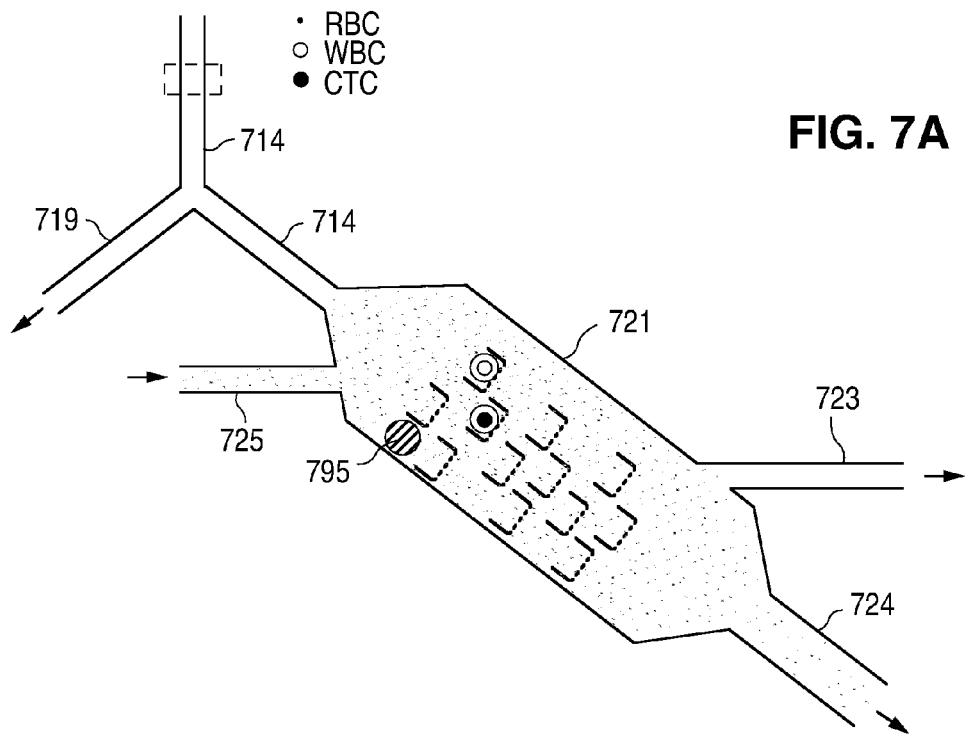
Figure 7B:
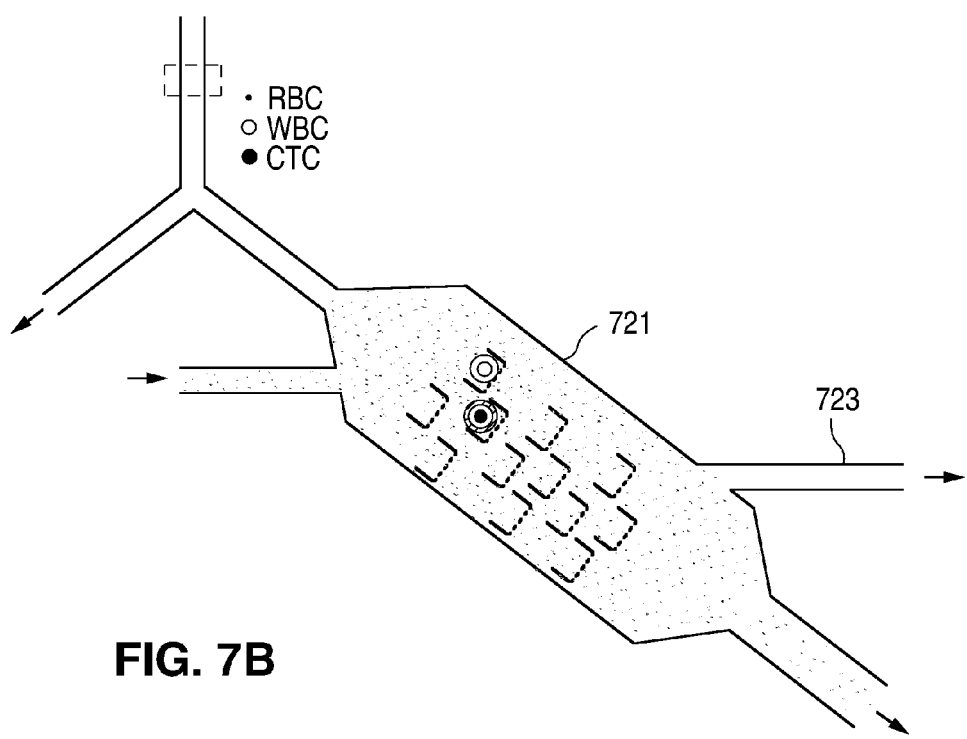

FIGS. 7A-7B show a circulating tumor cell (CTC) being moved into trapping segment collection channel 723 using an external electrode. In these figures, the electric field generated by the external electrode is indicated at 795. In FIG. 7A, the electric field is seen near a side wall of trapping chamber 721. The external electrode is translated across the penetrable wall of chamber 721 until electric field 795 acts upon the CTC (as seen in FIG. 7B). By translating the external electrode further across the penetrable wall of chamber 721, the CTC is moved to an area along a side of the chamber that is free of trapping structures (as seen in FIG. 7C) and then moved into collection channel 723 (as seen in FIG. 7D), where it may be moved through the channel by the electrode, or by pressure-driven flow or other means.

Collection channel 723 may be in fluid communication with a well disposed on a surface of the microfluidic device from which the target object is withdrawn for further processing or within which the object is further analyzed. Alternatively, the object may be delivered into an analysis module fabricated into or associated with the microfluidic device. For example, collection channel 723 may connect with channels and/or chambers within the microfluidic device, and further analysis may take place within these channels and/or chambers.

In another example, collection channel 723 may be in fluid communication with an analysis module attached or adjacent to the microfluidic device. In yet another example, collection channel 723 may be in fluid communication with (or may itself comprise) a tubular member such as a flexible tube, a rigid tube, a capillary, or a cannula that extends out from the microfluidic device to deposit the target object(s) onto a slide or into a multiwell plate. Further analysis of each object outside trapping chamber 721 may involve FISH, qPCR, digital PCR, electrophoresis, cell culture (e.g., for protein analysis), and other methods.

If the target objects typically comprise a very small percentage of the total number of objects in a sample, the concentration of these objects may be increased using methods such as aliquot-based, immunocapture-based, and size/shape/deformation-based physical enrichment methods. The enrichment may take place either before the objects are introduced into the microfluidic device or after the objects are introduced into the microfluidic device but before the objects are detected in the primary detection area seen, for example, at 172 in FIG. 1. Increasing the concentration of the target objects prior to primary detection can result in improved sensitivity and speed of extracting the target objects from a sample.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A microfluidic device for extracting target objects from a sample comprising:
   an aliquotting segment comprising a sample inlet channel, a first buffer inlet channel, a sample waste channel, and an aliquot delivery channel fluidly coupled at a fluid junction, the sample inlet channel and first buffer inlet channel in fluid communication with an inlet end of the fluid junction and the sample waste channel and aliquot delivery channel in fluid communication with an outlet end of the fluid junction, the aliquotting segment further comprising a second buffer inlet channel and a normally open valve, the second buffer inlet channel coupled to the fluid junction between the sample inlet channel and the sample waste channel, and the normally open valve operably coupled to the second buffer inlet channel; and a trapping segment in fluid communication with the aliquotting segment, the trapping segment comprising a trapping chamber, a plurality of trapping structures, a collection channel, and a waste channel, wherein the trapping structures are disposed in the trapping chamber, and wherein the collection channel and the waste channel are in fluid communication with the trapping chamber.

2. The microfluidic device of claim 1 wherein the aliquotting segment further comprises a third buffer inlet channel coupled to the first buffer inlet channel.

3. The microfluidic device of claim 1 wherein the aliquotting segment further comprises an aliquot disposal channel coupled to the aliquot delivery channel.

4. The microfluidic device of claim 1 wherein the first and second buffer inlet channels are in fluid communication with a buffer source.

5. The microfluidic device of claim 1 wherein the normally open valve comprises a valve structure formed across the width of the second buffer inlet channel and a deformable material disposed over at least a portion of the second buffer inlet channel in the area of the valve structure, wherein the deformable material is sealed over the second buffer inlet channel portion except in the area of the valve structure, thereby forming a covered second buffer inlet channel portion that permits fluid to flow over the valve structure.

6. The microfluidic device of claim 1 wherein the trapping segment further comprises a fluid inlet channel in fluid communication with the trapping chamber.

7. The microfluidic device of claim 1 wherein the trapping structures are constructed of a material that is hydrophobic.

8. The microfluidic device of claim 1 wherein a passage is provided within the trapping chamber to permit trapped objects to be manipulated through the passage.

9. The microfluidic device of claim 1 wherein an external wall of the trapping chamber is optically transparent.

10. The microfluidic device of claim 1 wherein an external wall of the trapping chamber comprises a material that is penetrable by an electric field generated external to the device, the electric field thereby capable of extending through the material and into the chamber.

11. The device of claim 10 wherein the external wall of the trapping chamber comprises an anisotropically conducting material.

12. The microfluidic device of claim 1 wherein the microfluidic device comprises a channel layer and a cover layer.

13. The microfluidic device of claim 12 wherein the cover layer is affixed to the channel layer except in an area of the microfluidic device within which the normally open valve is disposed.

* * * * *